(12) United States Patent
Morrison et al.

(10) Patent No.: US 8,317,755 B2
(45) Date of Patent: Nov. 27, 2012

(54) DEVICE FOR SECURING MEDICAL TUBING

(76) Inventors: David A. Morrison, Bellevue, NE (US);
Kristen K. Taenzler, Bellevue, NE (US)

( * ) Notice: Subject to any disclaimer, the term of this patent is extended or adjusted under 35 U.S.C. 154(b) by 285 days.

(21) Appl. No.: 12/659,578

(22) Filed: Mar. 12, 2010

(65) Prior Publication Data

US 2010/0292649 A1 Nov. 18, 2010

Related U.S. Application Data

(60) Provisional application No. 61/213,218, filed on May 18, 2009.

(51) Int. Cl.
*A61M 5/32* (2006.01)
(52) U.S. Cl. ........................................................ 604/180
(58) Field of Classification Search .................. 604/174, 604/177, 180
See application file for complete search history.

(56) References Cited

U.S. PATENT DOCUMENTS

| | | | | |
|---|---|---|---|---|
| 3,288,136 A | * | 11/1966 | Lund ............................. | 604/180 |
| 3,430,300 A | * | 3/1969 | Doan ............................. | 24/304 |
| 3,834,380 A | * | 9/1974 | Boyd ............................. | 604/180 |
| 4,074,397 A | | 2/1978 | Rosin | |
| 4,142,527 A | * | 3/1979 | Garcia .......................... | 604/180 |
| 4,324,236 A | * | 4/1982 | Gordon et al. ................ | 604/272 |
| 4,490,141 A | * | 12/1984 | Lacko et al. .................. | 604/180 |
| 4,583,976 A | * | 4/1986 | Ferguson ...................... | 604/180 |
| 4,702,736 A | * | 10/1987 | Kalt et al. ..................... | 604/180 |
| 4,726,716 A | * | 2/1988 | McGuire ....................... | 604/180 |
| 4,737,143 A | * | 4/1988 | Russell ......................... | 604/180 |
| 4,738,662 A | * | 4/1988 | Kalt et al. ..................... | 604/180 |
| 4,822,342 A | | 4/1989 | Brawner | |
| 4,976,700 A | * | 12/1990 | Tollini .......................... | 604/180 |
| 5,037,397 A | | 8/1991 | Kalt et al. | |
| 5,098,399 A | | 3/1992 | Tollini | |
| 5,135,506 A | * | 8/1992 | Gentelia et al. .............. | 604/180 |
| 5,147,322 A | | 9/1992 | Bowen et al. | |
| 5,304,146 A | | 4/1994 | Johnson et al. | |
| 5,397,639 A | | 3/1995 | Tollini | |
| 5,785,690 A | * | 7/1998 | Newman et al. .............. | 604/180 |
| 5,797,884 A | | 8/1998 | Byrd | |
| 5,833,633 A | * | 11/1998 | Sarvazyan .................... | 600/587 |
| 6,015,119 A | | 1/2000 | Starchevich | |
| 6,419,660 B1 | | 7/2002 | Russo | |
| 6,436,073 B1 | * | 8/2002 | Von Teichert ................. | 604/174 |

(Continued)

FOREIGN PATENT DOCUMENTS

JP 6-233824 A 8/1994

*Primary Examiner* — Kevin C Sirmons
*Assistant Examiner* — William Carpenter
(74) *Attorney, Agent, or Firm* — Richard C. Litman

(57) ABSTRACT

The device for securing medical tubing is an attachment for use with medical tubing, such as a nasal cannula, nasogastric/orogastric tubes or the like, that permits the medical tubing to be comfortably and releasably secured to the skin of the patient. The device for securing medical tubing includes a base having opposed inner and outer surfaces. Laterally opposed peripheral edges of the first surface of the base are releasably secured to one another to form a channel for receiving and releasably securing a portion of the medical tubing. The outer surface of the base is divided into an attachment portion adapted for releasable attachment to the patient's skin, and an outwardly facing portion. Preferably, a layer of non-allergenic adhesive is applied to the attachment portion of the outer surface. The adhesive layer may be covered by a release strip.

6 Claims, 3 Drawing Sheets

U.S. PATENT DOCUMENTS

| | | |
|---|---|---|
| 6,565,537 B2 | 5/2003 | Tollini |
| 6,827,706 B2 * | 12/2004 | Tollini ............................ 604/180 |
| D608,444 S * | 1/2010 | Kyvik et al. ................... D24/130 |
| D663,834 S * | 7/2012 | Kyvik et al. ................... D24/128 |
| 2002/0143296 A1 | 10/2002 | Russo |
| 2002/0156423 A1 | 10/2002 | Tollini |
| 2006/0180154 A1 | 8/2006 | Stone |
| 2007/0235034 A1 | 10/2007 | Weaver |
| 2007/0289597 A1 | 12/2007 | Masella et al. |
| 2008/0071224 A1 | 3/2008 | Forsyth |
| 2008/0190435 A1 | 8/2008 | Hansen |
| 2008/0221526 A1 * | 9/2008 | Fleischer ....................... 604/180 |
| 2009/0054844 A1 | 2/2009 | Alyea et al. |

\* cited by examiner

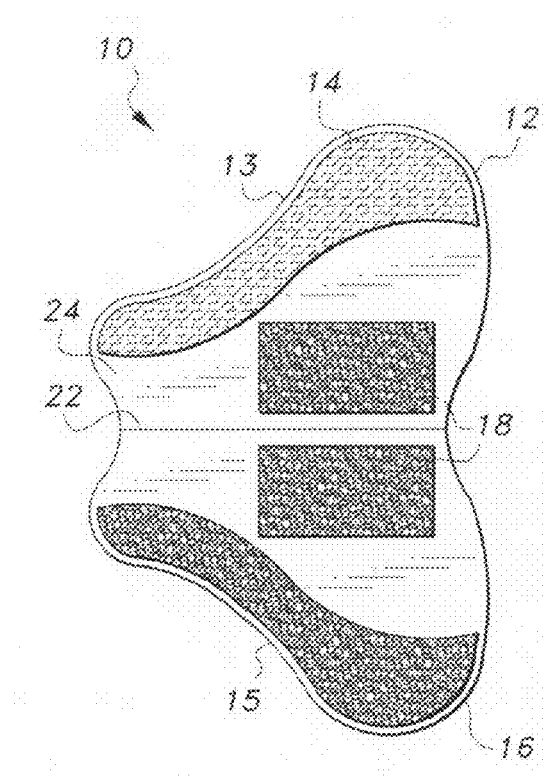
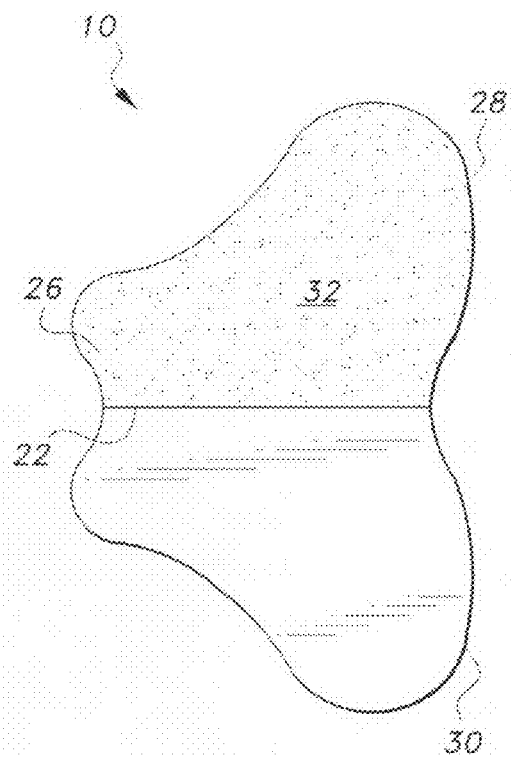
Fig. 2  Fig. 3
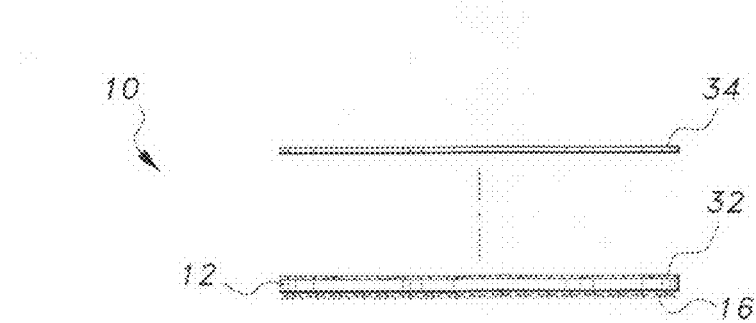
Fig. 4

DEVICE FOR SECURING MEDICAL TUBING

CROSS-REFERENCE TO RELATED APPLICATION

This application claims the benefit of U.S. Provisional Patent Application Ser. No. 61/213,218, filed May 18, 2009.

BACKGROUND OF THE INVENTION

1. Field of the Invention

The present invention generally relates to flexible tubing, particularly medical tubing, and more particularly to a device for securing medical tubing to the skin of the patient.

2. Description of the Related Art

Nasal cannulae, nasogastric/orogastric tubes and other forms of medical tubing are commonly used medical devices for providing oxygen and nourishment to patients. Stabilization of such tubing is important because if the tubing is not properly secured to the patient, lateral movement or awkward positioning of the tubing can irritate the patient's nostrils or skin, particularly when the tubing is in place for several days or weeks. Further, retraction or advancement of the tubing must be prevented, because inadvertent retraction of a feeding tube, for example, can cause the tube to retreat to the esophagus where it can dispense fluid into the lungs.

Similarly, inadvertent retraction of a gastric decompression tube can cause the tube to apply suction to sensitive esophageal tissues. Proper positioning of a nasogastric tube, for example, is often insured by initially taking an x-ray of the patient. Thus, once properly positioned, it is wasteful in terms of time and resources to reposition the tube if it is not properly stabilized.

Commonly, nasogastric tubes are stabilized simply by taping the tube to the face of the patient. This often results in improper positioning of the tube, thereby irritating the patient's nostrils and/or facial skin. The direct application of medical tape to the patient's skin also tends to cause irritation, especially when removing the tape. Further, medical tape is difficult and time consuming to apply and remove. Nasal airway tubes are also stabilized simply by taping the nose or face. In addition to nasal tubes, there is also a need to secure and stabilize various tubes over other areas of a patient's body, such as intravenous tubes, gastronomy tubes, catheters, and the like. Thus, a device for securing medical tubing solving the aforementioned problems is desired.

SUMMARY OF THE INVENTION

The device for securing medical tubing is an attachment for use with medical tubing, such as a nasal cannula, nasogastric/orogastric tubes or the like, that allows the medical tubing to be comfortably and releasably secured to the skin of the patient. The device for securing medical tubing includes a base having opposed inner and outer surfaces. The base is preferably formed from a water-resistant, flexible and non-allergenic/non-irritating material.

Laterally opposed peripheral edges of the first surface of the base are releasably secured to one another by any suitable type of releasable peripheral fastener, such as hook and loop fasteners. When the laterally opposed peripheral edges are secured together, the base defines a channel for receiving and releasably securing a portion of the medical tubing. The portion of medical tubing is preferably also releasably secured to a central portion of the inner surface of the base by any suitable type of releasable central fastener, such as a hook and loop fastener.

The outer surface of the base is divided into an attachment portion, adapted for releasable attachment to the patient's skin, and an outwardly facing portion. Preferably, a layer of non-allergenic adhesive is applied to the attachment portion of the outer surface. The adhesive layer may be covered by a release strip.

These and other features of the present invention will become readily apparent upon further review of the following specification and drawings.

BRIEF DESCRIPTION OF THE DRAWINGS

FIG. 2 is a plan view of the inner surface of the device for securing medical tubing according to the present invention.

FIG. 3 is a plan view of the opposite outer surface of the device of FIG. 2.

FIG. 4 is a side view of the device for securing medical tubing according to the present invention, the release paper being shown exploded from the adhesive surface.

Similar reference characters denote corresponding features consistently throughout the attached drawings.

DETAILED DESCRIPTION OF THE PREFERRED EMBODIMENTS

Figure 1:
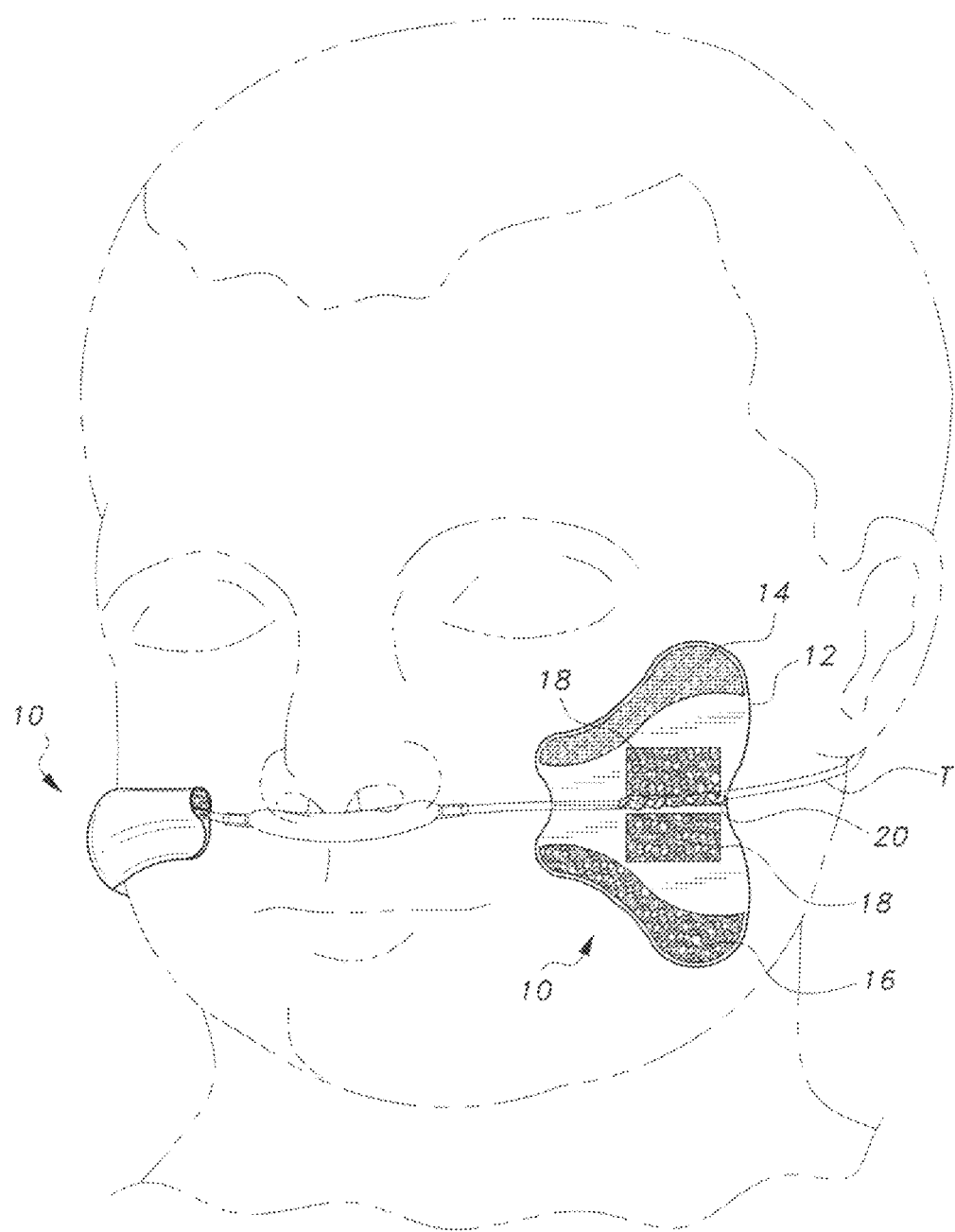
FIG. 1 is an environmental, perspective view of a device for securing medical tubing according to the present invention, shown securing a nasal cannula to a patient's face, one device being shown on the right cheek in a closed position and a second device being shown on the left cheek in an open position to show details thereof.

Referring to FIG. 1, the device for securing medical tubing 10 is an attachment for use with medical tubing, such as a nasal cannula, a nasogastric or orogastric tube, or the like, that permits the medical tubing to be comfortably and releasably secured to the skin of the patient. In FIG. 1, it should be understood that tubing T is shown for exemplary purposes only, and that the device 10 may be used with any type of medical tubing.

As best shown in FIGS. 2 and 3, the device for securing medical tubing 10 includes a base 12 having opposed inner and outer surfaces 24, 26, respectively. The base 12 is preferably formed from a water-resistant sheet of flexible and non-allergenic/non-irritating material, such as those typically used for water-resistant bandages. It should be understood that the butterfly shape and relative dimensions of the base 12 illustrated in FIGS. 1-3 are shown for exemplary purposes only. Base 12 may have any desired shape or dimensions, depending upon the type of tubing T to be held, and on the portion of the body to which the base 12 is applied.

As best shown in FIG. 2, laterally opposed peripheral edges 13, 15 of the inner surface 24 of the base 12 are releasably secured to one another by any suitable type of releasable fastener, such as exemplary hook and loop fasteners 14, 16. Hook and loop fasteners 14, 16 may be secured to the peripheral edges 13, 15 by adhesive, stitching, heat or ultrasonic bonding, or the other suitable attachment method.

FIG. 1 illustrates both open and closed devices 10. When the laterally opposed peripheral edges 13, 15 of base 12 are fastened together, the base 12 defines a channel for receiving and releasably securing a portion of the medical tubing T. The portion of medical tubing T is preferably releasably secured within a central portion of the first surface 24 of the base 12 by any suitable type of releasable fastener, such as a hook and loop fastener. As shown in FIG. 2, a central fold line 22 is preferably formed along a central, longitudinal axis of base 12. When folded, the medical tubing T is positioned against fold line 22. As shown in FIG. 2, hook material 18, for example, is preferably secured to the inner surface 24 of base 12 adjacent to, and on one or both sides, of the fold line 22. Loop material 20, as shown in FIG. 1, for example, may be wrapped around and attached to the medical tubing T, e.g., by adhesive, to form a tubing fastener. When the tubing T is received within the channel formed by the folded base 12, and positioned against fold line 22, the hook and loop fastener 18, 20 releasably secures the tubing T within the channel. Thus, tubing T is preferably retained within the device both by mating peripheral fasteners 14, 16 and mating central fasteners 18, 20.

As shown in FIG. 3, the outer surface 26 of the base 12 is divided into an attachment portion 28 adapted for releasable attachment to the patient's skin, and an outwardly facing portion 30. Preferably, a layer of non-allergenic and non-comedogenic adhesive 32 is applied to the attachment portion 28 of the outer surface 26. As shown in FIG. 4, the adhesive layer 32 may be covered by a release strip 34. Such adhesives and release strips are well known in the art of bandages and skin dressings, and it should be understood that any suitable type of adhesive and release strip may be utilized.

When folded, the medical tubing T is secured within the channel formed by folded base 12, the attachment portion 28 is releasably secured to the patient's skin (as shown in FIG. 1), the outwardly-facing portion 30 of the outer surface 26 provides water-resistant protection for the medical tubing T (which is further easily cleanable), and the overall device 10 provides an easily-removable means for securing and stabilizing the medical tubing T. The hook and loop fasteners 14, 16 and 18, 20 allow for ease in removal, replacement and adjustment of the medical tubing T in the device 10.

Figure 5:
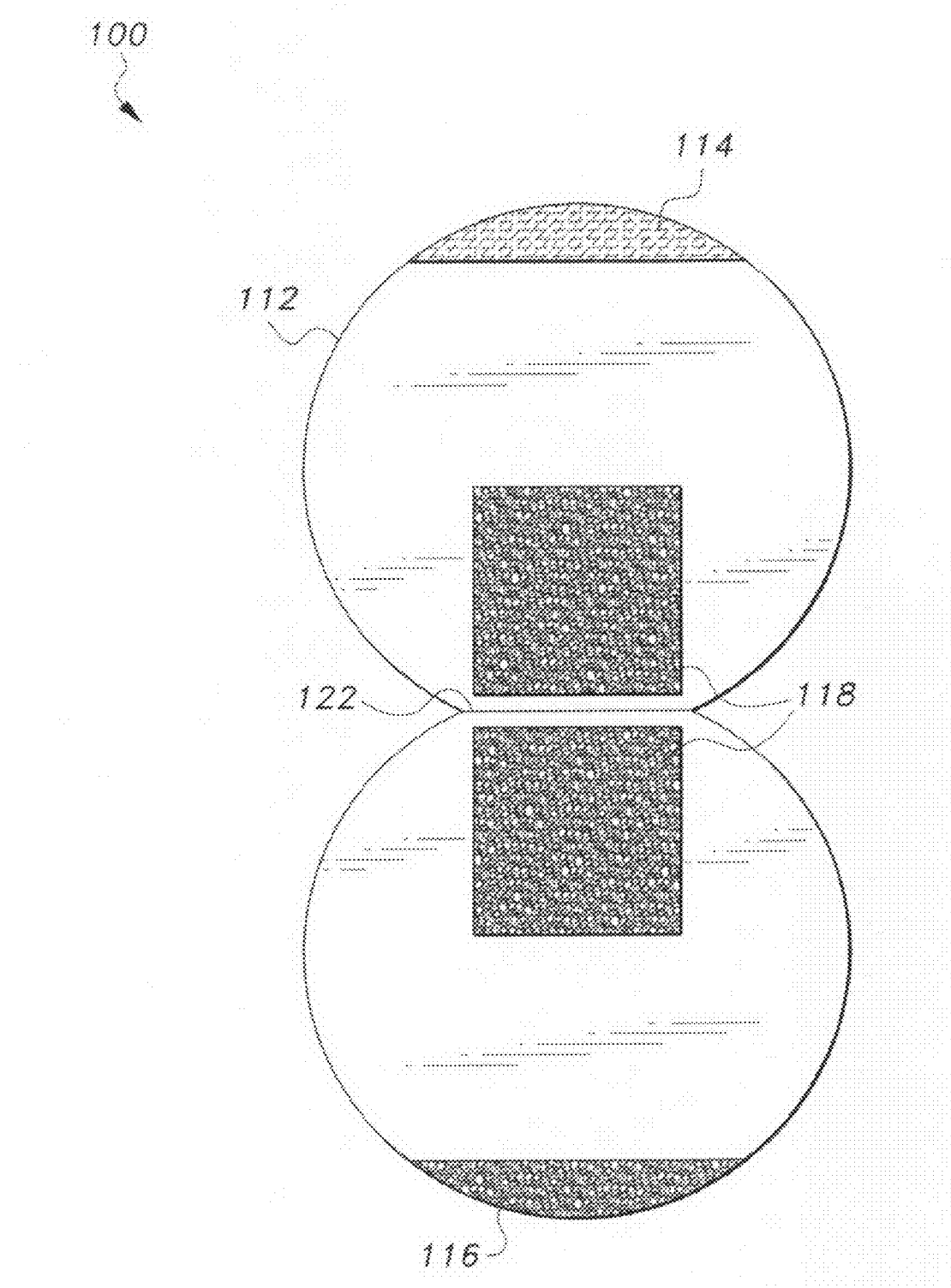
FIG. 5 is a plan view of an alternative embodiment of a device for securing medical tubing according to the present invention.

As noted above, the base may be sized or shaped in any desired configuration. FIG. 5 illustrates an alternative embodiment in which the device 100 includes a base 112 having peripheral hook and loop fasteners 114, 116 mounted on an inner surface thereof, but with additional or more extensive hook fastener material 118 secured thereto about the central fold line 122 (similar to base 12, hook and loop fasteners 14, 16, hook material 18 and fold line 22 of device 10). The base 112 is formed in two substantially circular portions, which are symmetric about the central fold line 122. It should be understood that this alternative configuration is shown for exemplary purposes only, and that the base of the device may have any desired shape or dimensions, depending upon the type of tubing T the device will be used with, and upon the portion of the patient's body to which tubing T will be attached. Additionally, it should be understood that the device for securing medical tubing may be manufactured in a variety of different sizes for use with, for example, infants, children and adults.

It is to be understood that the present invention is not limited to the embodiments described above, but encompasses any and all embodiments within the scope of the following claims.

We claim:

1. A device for securing medical tubing, comprising:
    a base having opposed inner and outer surfaces, the base further having a central fold line formed therein for defining a channel adapted for receiving and releasably securing a portion of medical tubing passing through the channel, wherein the base is configured into a substantially butterfly-shaped contour defining:
        i) a curved bottom edge having a first length, an opposed curved top edge having a second length wherein the second length is greater than the first length; and
        ii) opposing curved side edges of substantially equal length;
    mating peripheral fasteners disposed on the inner surface of the base contiguous to the side edges for releasably securing laterally opposed peripheral edges of the inner surface of the base together, wherein said peripheral fasteners comprise non-adhesive fasteners,
    at least one central fastener attached to the inner surface of the base adjacent the central fold line, the at least one central fastener being adapted for attachment to the medical tubing, the at least one central fastener releasably securing the portion of medical tubing within the channel; and
    an adhesive layer formed on a portion of the outer surface of the base, the adhesive layer being adapted for releasably securing the outer surface of the base to a patient's skin.

2. The device for securing medical tubing as recited in claim 1, wherein said base is formed from a sheet of water-resistant, flexible material.

3. The device for securing medical tubing as recited in claim 1, wherein said non-adhesive fasteners comprise mating hook and loop fasteners.

4. The device for securing medical tubing as recited in claim 1, further comprising a tubing fastener adapted for being secured to the portion of medical tubing passing through the channel.

5. The device for securing medical tubing as recited in claim 4, wherein the at least one central fastener and the tubing fastener comprise mating hook and loop fasteners.

6. The device for securing medical tubing as recited in claim 1, further comprising a release strip releasably covering the adhesive layer.

* * * * *